United States Patent [19]

Kaimer

[11] Patent Number: 5,143,061
[45] Date of Patent: Sep. 1, 1992

[54] SUPPLEMENTAL SEAL FOR OXYGEN MASK

[76] Inventor: Stephen F. Kaimer, 5871 Long Spurling, Pleasant Plain, Ohio 45162

[21] Appl. No.: 730,220

[22] Filed: Jul. 15, 1991

Related U.S. Application Data

[63] Continuation of Ser. No. 568,846, Aug. 17, 1990, abandoned.

[51] Int. Cl.⁵ .......................... A62B 18/08; A62B 9/02
[52] U.S. Cl. ........................... 128/206.24; 128/206.25; 128/205.25
[58] Field of Search ....................... 128/205.25, 206.21, 128/206.24, 206.25, 206.26

[56] References Cited

U.S. PATENT DOCUMENTS

| | | | |
|---|---|---|---|
| 2,634,724 | 4/1953 | Burns | 128/206.19 |
| 3,052,887 | 9/1962 | Sockel et al. | 128/206.24 |
| 3,330,274 | 7/1967 | Bennett | 128/206.26 |
| 4,797,956 | 1/1989 | Boyce | 128/206.19 |
| 4,907,584 | 3/1990 | McGinnis | 128/206.24 |
| 4,966,140 | 10/1990 | Herzberg | 128/206.24 |
| 4,974,574 | 8/1990 | Dagher | 128/863 |

FOREIGN PATENT DOCUMENTS

| | | | |
|---|---|---|---|
| 428338 | 5/1935 | United Kingdom | 128/206.24 |
| 837250 | 6/1960 | United Kingdom | 128/206.24 |
| 848215 | 9/1960 | United Kingdom | 128/206.24 |
| 8803036 | 5/1988 | World Int. Prop. O. | 128/206.24 |

*Primary Examiner*—Edgar S. Burr
*Assistant Examiner*—Kimberly L. Asher
*Attorney, Agent, or Firm*—Wood, Herron & Evans

[57] ABSTRACT

An adhesively backed strip of foam or sponge rubber is adapted to be removably secured within the upper peripheral edge of a conventional oxygen mask used to deliver oxygen to a patient. The adhered strip fills up the otherwise void spaces between the face of the patient and the peripheral edge of the mask, thereby preventing leakage of pressurized oxygen toward the eyes of a patient during oxygen delivery.

6 Claims, 1 Drawing Sheet

SUPPLEMENTAL SEAL FOR OXYGEN MASK

This is a continuation of application Ser. No. 07/568,846, filed Aug. 17, 1990, now abandoned.

FIELD OF THE INVENTION

This invention relates to a supplemental seal attachable to a conventional oxygen mask to prevent oxygen leakage when the mask is worn.

BACKGROUND OF THE INVENTION

Oxygen delivery systems are often used in a hospital environment to assist patients suffering from impaired breathing or to assist in the administration of drugs to the patient, or simply to assure an oxygen rich breathing supply. A typical oxygen delivery system includes an oxygen source that supplies pressurized oxygen via a tube to a bag that communicates with the inside of a face mask. The face mask engages and encloses the face of the patient during oxygen delivery. These masks are usually made of molded plastic and include an elastic strap for maintaining a secured position on the face.

For sanitary reasons, the oxygen masks used in most oxygen delivery systems are discarded after use by a single individual. At times, for the same reason, more than one mask is used by the same individual. As a result, the conventional oxygen masks designed to be used with these systems are generally manufactured as a relatively inexpensive, "one size fits all" item.

While use of a single conventional size mask reduces hospital inventory and minimizes production costs, these economic advantages are achieved at the expense of the patient's comfort. For many patients, the flexible peripheral edge of the mask simply does not conform adequately to the face during oxygen delivery, particularly between the bridge of the nose and the cheeks. As a result, during oxygen delivery, pressurized oxygen gas leaks between the edge of the mask and the cheeks of the subject into the eyes, and it causes drying of the fluids on the surface of the eyes, resulting in a great deal of discomfort for the patient.

Moreover, leaked oxygen represents an additional cost that must be borne by the hospital and eventually passed on to the patient.

There exists a genuine need to eliminate the oxygen leakage from within the inside of a conventional oxygen mask during oxygen delivery.

SUMMARY OF THE INVENTION

This invention contemplates a supplemental rubber seal adapted to be secured inside the soft peripheral edge of a conventional oxygen mask. The rubber seal is adapted to occupy the otherwise open spaces between the face of a subject and the peripheral edge of the mask along the upper half of the mask, where pressurized oxygen is most likely to leak from the mask toward the patient's eyes.

According to a preferred embodiment of the invention, the supplemental seal is made of a foam rubber strip that is rectangular in cross-sectional shape and about 7" long. An adhesive backing is applied to one side of the foam rubber length. The adhesive backing may be activatable by removal of a peel-away strip when it is desired to adhere the seal inside the upper peripheral edge of the mask. The exact location of the seal inside the mask will vary somewhat depending upon the shape of the patient's nose bridge and facial features.

These and other features of the invention will be more readily appreciated in view of the following detailed description and the drawings.

DETAILED DESCRIPTION OF THE DRAWINGS

Figure 1:
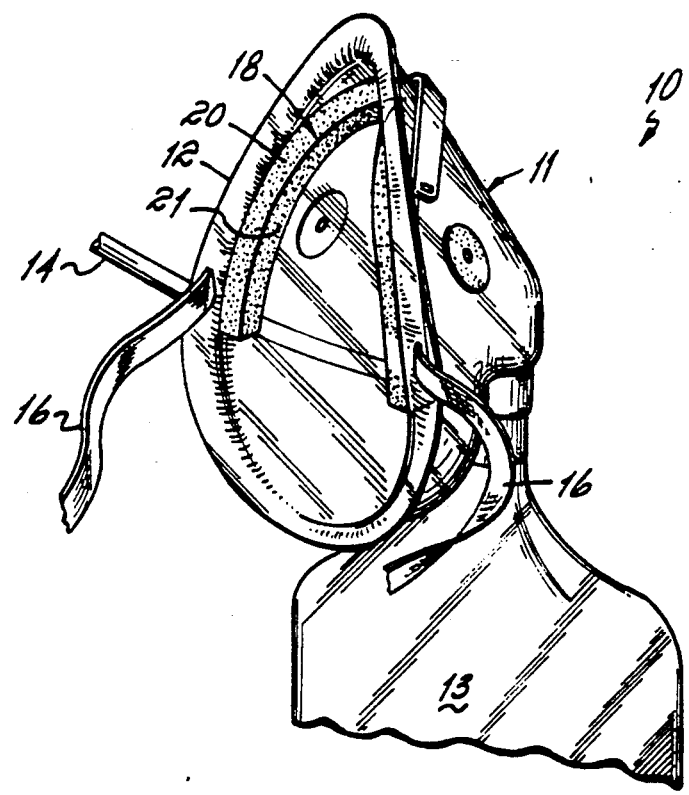
FIG. 1 is a perspective view of an oxygen delivery system including an oxygen mask equipped with a supplemental seal in accordance with a preferred embodiment of the invention.

FIG. 1 shows an oxygen delivery system 10 for use in delivering pressurized oxygen to a patient. The system includes a face mask 11 with a peripheral edge 12 adapted to substantially engage the face of a patient during oxygen delivery. Thus, peripheral edge 12 substantially engages the face of a patient about a first, outer perimeter. Oxygen is supplied to the inside of the mask 11 from pressurized oxygen supply (not shown) to a bag 13 via a tube 14. The bag 13 is in fluid communication with the inside of the mask 11. An elastic strap 16 connects to opposite sides of the mask 11 to hold it in secured position upon the head of a patient during oxygen delivery.

FIG. 1 also shows a strip 18 of foam rubber secured inside the upper portion of peripheral edge 12 of the mask 11. The strip 18 substantially engages the face of the patient about a second, inner perimeter which is removed inwardly from the first outer perimeter formed by edge 12. The strip 18 serves as a supplemental seal for the mask 11 at the location where leakage is most likely to occur and where leakage is most likely to cause the greatest amount of discomfort to the patient. A rearwardly directed side 20 and an internally directed side 21 will contact the face of a patient when the mask is in position. An externally directed side 22 (shown in FIG. 2), i.e., the side opposite from the internally directed side 21, is supplied with an adhesive backing for securement to the mask 11. The strip or seal 18 is preferably rectangular in cross-section with dimensions of about ⅜" from the internal side to the external side, about ¼" from the forward to the rearward side and a length of about 7", although dimensional variation may be desirable, depending upon the shape of the face. These seals 18 may be formed by cutting the strips at desired lengths from a large pad or section of foam rubber or stamping them from a pad. While strip 18 has been described as being made from foam rubber, it is to be understood that strip 18 could also be formed of soft-molded plastic, or any other "cushioning" or deformable material. In some instances, it may be desirable to use "non-allergenic" material.

Figure 2:
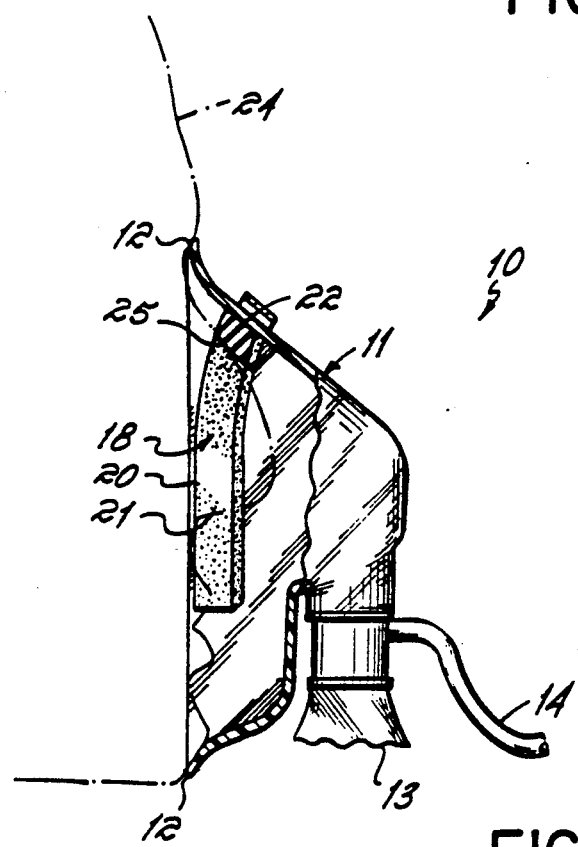
FIG. 2 is a side view, partially in cross-section, of an oxygen mask contacting a subject's face during oxygen delivery, the mask equipped with a supplemental seal in accordance with a preferred embodiment of the invention.

FIG. 2 shows the mask 11 in position upon the face of a patient 24, with edge 12 in substantial peripheral contact with the face. When secured to the mask 11, the top of seal 18 preferably contacts the bridge of the nose 25 of a patient 24. This provides cushioned engagement of the mask 11 to the face during use. From this upper position, the opposite sides of the seal 18 extend downwardly in a common vertical plane. Because the seal 18 is of foam or sponge rubber, it conforms to provide a comfortable fit in the areas where there is already a close fit between the face and the upper portion of the edge 12. Moreover, the rubber strip 18 is large enough to occupy voids that would otherwise be located in the areas where the face and the upper portion of the edge 12 of the mask 11 are not in close contact, i.e., where pressurized oxygen gas tends to leak toward the eyes.

While the location of the strip 18 is referred to as "inside" the peripheral edge 12, it is to be understood that the invention contemplates locating the strip 18 on the mask 11 so that it contacts the bridge of a patient's nose. Depending upon the size and shape of the patient's face, the top of the strip 18 may be anywhere from $\frac{1}{8}$" to 1 and $\frac{1}{4}$" from the uppermost portion of the mask 11.

After oxygen delivery, the mask 11 and strip 18 may be discarded together. Alternately, if desired, or if a particularly comfortable fit is achieved, the strip 18 may be removed for reuse by the same patient with another mask.

While a preferred embodiment of the invention has been described, it is to be understood that the invention is not limited thereby and that in light of the present disclosure of the invention, various other alternative embodiments will be apparent to one of ordinary skill in the art. Accordingly, it is to be understood that changes may be made without departing from the scope of the invention as particularly set out and claimed.

I claim:

1. A method of delivering oxygen to a patient with a leak-proof oxygen mask comprising the steps of:
    providing a conventional oxygen mask having a peripheral sealing edge and a nose surrounding upper portion;
    customizing the conventional oxygen mask to the face of a patient by,
    (a) providing a strip of foam rubber having a length equal to approximately one-half of the circumference of said peripheral sealing edge,
    (b) spacing said foam rubber strip inwardly of said peripheral sealing edge of said mask in said upper nose surrounding portion, locating said foam rubber in a position which will overlie the bridge of the patient's nose when the conventional oxygen mask is worn by the patient,
    (d) adhesively attaching said foam rubber strip to said mask at said inwardly located position in said nose surrounding upper portion, thereby to provide cushioned engagement of said mask to the patient's face; and
    (e) delivering oxygen to the patient via said customized mask.

2. The method of claim 1 wherein the strip of foam rubber has a rectangularly shaped cross-section.

3. The method of claim 1 and further comprising the step of:
    discarding said mask and said strip after oxygen delivery.

4. The method of claim 1 and further comprising the steps of:
    removing said foam rubber strip from said mask;
    discarding said mask;
    providing a second mask;
    customizing said second mask by,
    (a) attaching said foam rubber strip to said second mask according to steps (b), (c) and (d) of claim 23; and
    delivering oxygen to the patient via said second customized mask.

5. In an oxygen delivery system which includes a conventional oxygen mask having a peripheral sealing edge with a nose surrounding upper portion and means for delivering oxygen to the patient via the mask, the improvement comprising:
    means for customizing said conventional oxygen mask to the face of the patient to provide a leak-proof seal therebetween during oxygen delivery to the patient, the means for customizing including a foam rubber strip adhesively attached to said conventional oxygen mask within said nose surrounding upper portion at a position spaced inwardly of said peripheral sealing edge of said mask so as to overlie the bridge of the patient's nose and provide cushioned engagement of said mask to the patient's face at the bridge of the nose when the mask is worn by the patient, thereby to prevent leakage of delivered oxygen in the direction of the eyes of the patient during oxygen delivery, said foam rubber strip having a length equal to approximately one-half the circumference of the peripheral sealing edge.

6. The oxygen delivery system of claim 5 wherein the strip of foam rubber is rectangular in shape.

* * * * *